(12) United States Patent
Chu et al.

(10) Patent No.: US 11,974,722 B2
(45) Date of Patent: May 7, 2024

(54) ENDOSCOPIC DEVICE WITH INTERCHANGEABLE SHAFT

(71) Applicant: BOSTON SCIENTIFIC SCIMED, INC., Maple Grove, MN (US)

(72) Inventors: Michael S. H. Chu, Brookline, MA (US); Sacha Tang, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 363 days.

(21) Appl. No.: 16/948,741

(22) Filed: Sep. 30, 2020

(65) Prior Publication Data

US 2021/0100429 A1 Apr. 8, 2021

Related U.S. Application Data

(60) Provisional application No. 62/911,749, filed on Oct. 7, 2019.

(51) Int. Cl.
*A61B 1/00* (2006.01)
*A61B 1/005* (2006.01)

(52) U.S. Cl.
CPC ........ *A61B 1/0057* (2013.01); *A61B 1/00124* (2013.01); *A61B 1/0016* (2013.01); *A61B 1/0052* (2013.01)

(58) Field of Classification Search
CPC . A61B 1/0057; A61B 1/0052; A61B 1/00133; A61B 1/0103; A61B 1/00066; A61B 1/00121; A61B 1/00112; A61B 17/00; A61B 1/00124; A61B 1/00105
USPC ........................................ 600/136, 137, 149
See application file for complete search history.

(56) References Cited

U.S. PATENT DOCUMENTS

| 4,919,112 | A | | 4/1990 | Siegmund | |
|---|---|---|---|---|---|
| 5,347,995 | A | * | 9/1994 | Slater | A61B 1/267 359/511 |
| 6,569,084 | B1 | * | 5/2003 | Mizuno | A61B 1/0051 600/102 |
| 6,626,826 | B1 | * | 9/2003 | Van Der Weegen | A61B 1/303 600/119 |
| 8,337,402 | B1 | * | 12/2012 | Ellis | A61B 1/267 600/199 |

(Continued)

FOREIGN PATENT DOCUMENTS

| WO | 97/28839 | 8/1997 |
|---|---|---|
| WO | 2008/048688 | 4/2008 |

*Primary Examiner* — Timothy J Neal
*Assistant Examiner* — James Edward Boice
(74) *Attorney, Agent, or Firm* — Bookoff McAndrews, PLLC

(57) ABSTRACT

An endoscopic device includes a handle body operatively couplable to a shaft housing. The handle body includes an actuator for controlling a distal end of an endoscopic shaft extending from the shaft housing. The device also includes a pull wire attachment configured to operatively couple to a pull wire extending through the shaft housing and the endoscopic shaft to the distal end. Applying tension to the pull wire deflects the distal end of the endoscopic shaft. In addition, the device includes a pulling mechanism coupled to the actuator and having the pull wire attachment extending therefrom. When the pull wire attachment is operatively coupled to the pull wire, actuation of the actuator applies tension to the pull wire and deflects the distal end of the endoscopic shaft.

19 Claims, 8 Drawing Sheets

(56) References Cited

U.S. PATENT DOCUMENTS

| | | | |
|---|---|---|---|
| 2001/0037050 A1* | 11/2001 | Lemperle | A61B 1/307 |
| | | | 600/135 |
| 2002/0133077 A1 | 9/2002 | Edwardsen et al. | |
| 2003/0233026 A1 | 12/2003 | Saadat et al. | |
| 2008/0214892 A1* | 9/2008 | Irion | A61B 1/05 |
| | | | 600/112 |
| 2008/0221391 A1* | 9/2008 | Weitzner | A61B 1/00154 |
| | | | 604/524 |
| 2009/0118618 A1* | 5/2009 | Harhen | A61B 8/445 |
| | | | 600/459 |
| 2009/0176185 A1* | 7/2009 | Chen | A61B 1/00052 |
| | | | 433/29 |
| 2011/0034775 A1* | 2/2011 | Lozman | A61B 17/1684 |
| | | | 600/204 |
| 2013/0184691 A1* | 7/2013 | Oskin | A61B 1/00128 |
| | | | 606/1 |
| 2014/0275763 A1* | 9/2014 | King | A61B 1/00105 |
| | | | 600/110 |
| 2015/0112141 A1 | 4/2015 | Oginski et al. | |
| 2015/0157387 A1* | 6/2015 | OuYang | A61B 1/3132 |
| | | | 606/34 |
| 2015/0164313 A1* | 6/2015 | Ouyang | A61B 1/00071 |
| | | | 600/103 |
| 2019/0246886 A1 | 8/2019 | Harada et al. | |
| 2020/0170701 A1* | 6/2020 | O'Keefe | A61B 17/00234 |
| 2020/0397232 A1* | 12/2020 | Ulmschneider | H04N 23/54 |
| 2021/0030394 A1* | 2/2021 | Caswell | A61B 8/4472 |
| 2021/0059506 A1* | 3/2021 | Wang | A61B 1/0051 |
| 2021/0068619 A1* | 3/2021 | Shin | A61B 1/00128 |
| 2021/0093166 A1* | 4/2021 | Shin | A61B 1/0052 |

\* cited by examiner

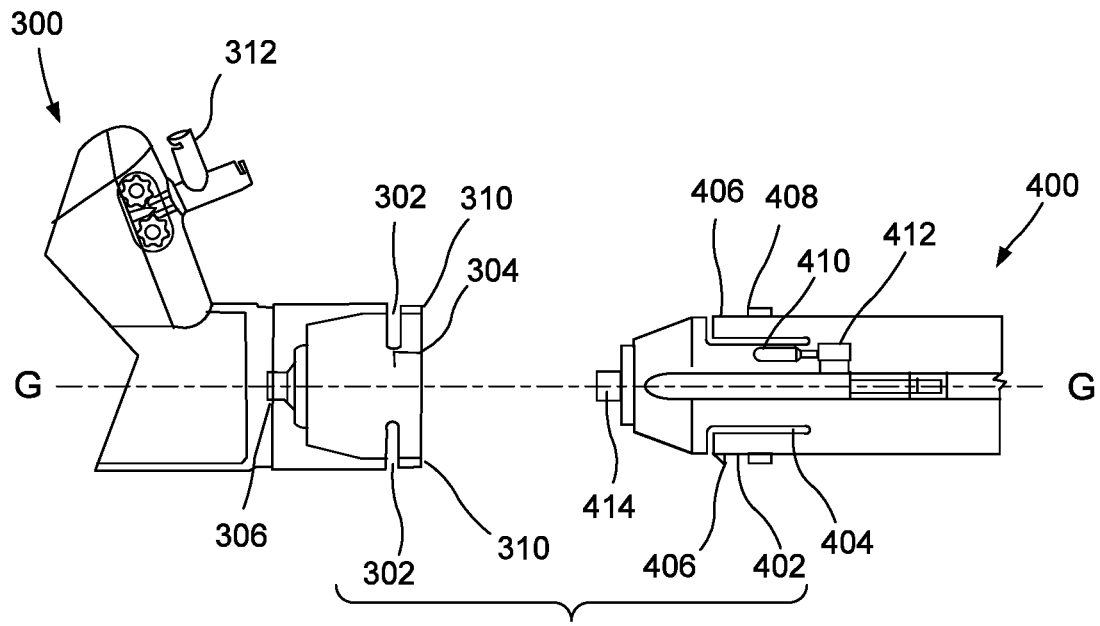
F I G. 4A
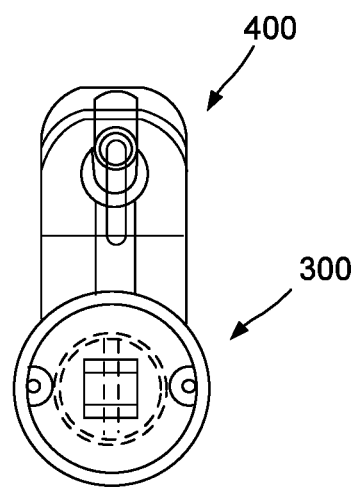
F I G. 4B

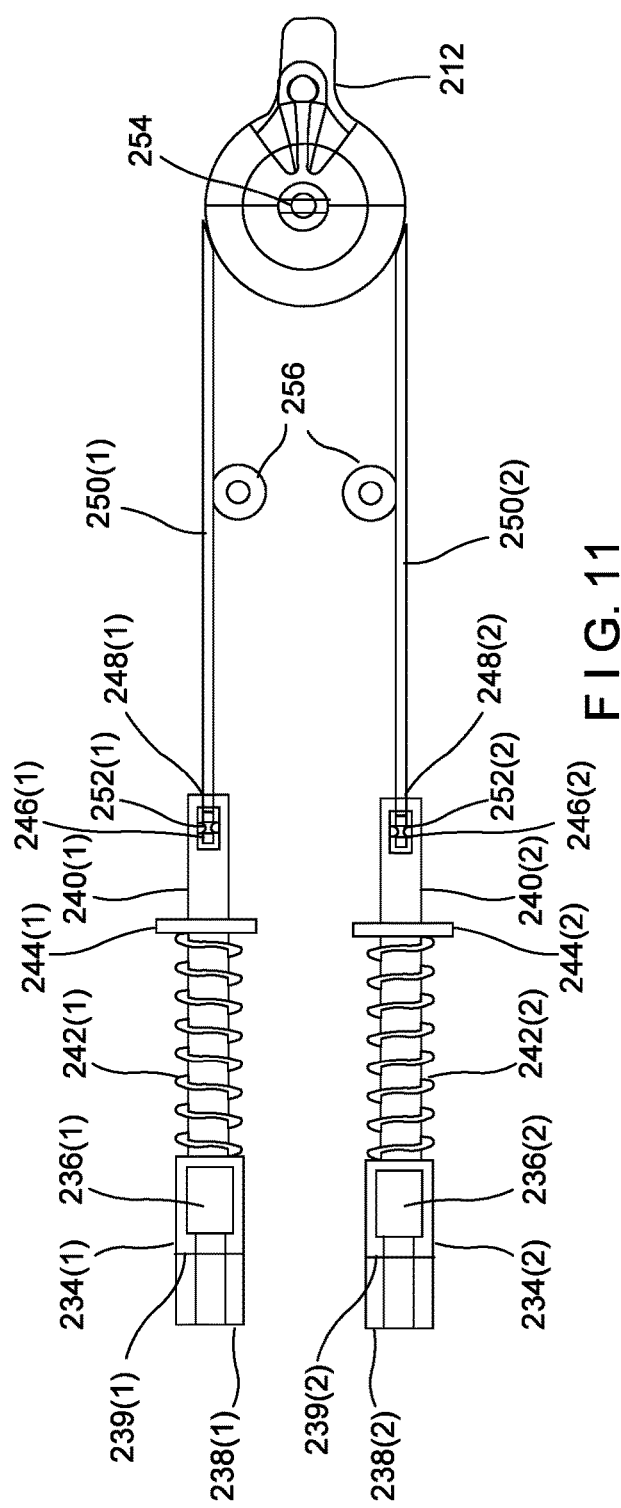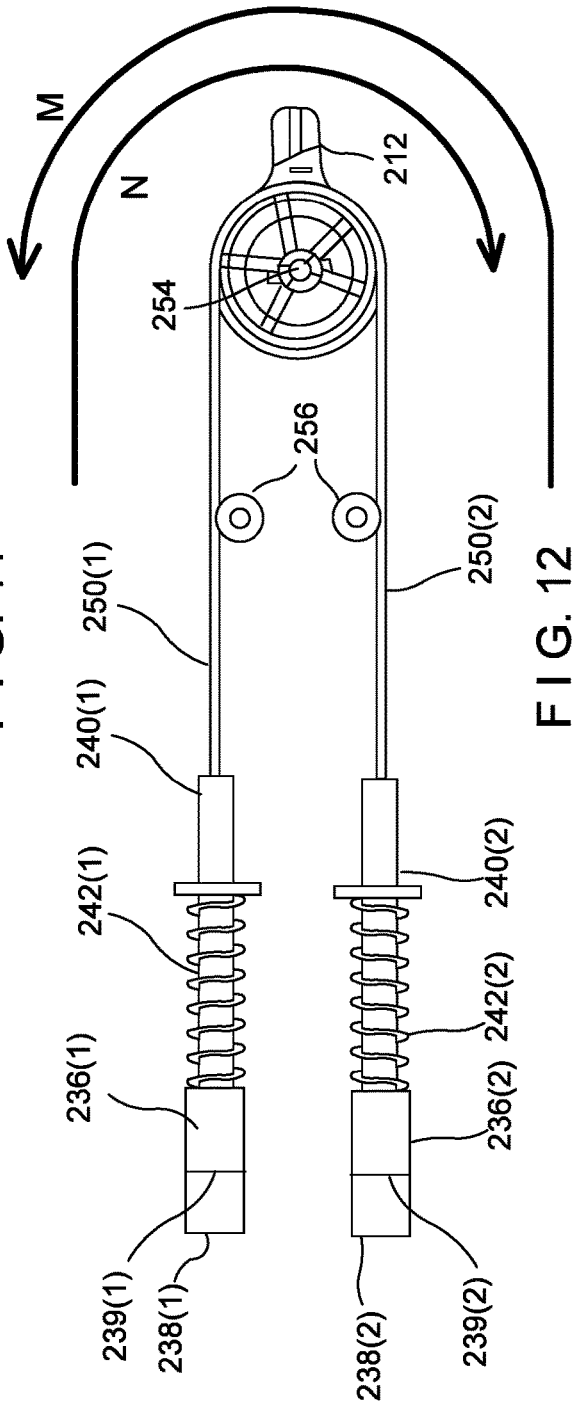
FIG. 11
FIG. 12

ENDOSCOPIC DEVICE WITH INTERCHANGEABLE SHAFT

PRIORITY CLAIM

The present disclosure claims priority to U.S. Provisional Patent Application Ser. No. 62/911,749 filed Oct. 7, 2019; the disclosure of which is incorporated herewith by reference.

FIELD

The present disclosure relates to an endoscopic device with separate shaft and handle portions that are selectively couplable (physically and electrically) to one another.

BACKGROUND

As understood by those skilled in the art, endoscopes may include a flexible or rigid shaft coupled to a handle including controls and interfaces for other equipment. Control of an endoscope may be implemented via actuators (e.g., button, deflection knobs, etc.) on the handle to deflect a distal tip of the flexible shaft, thereby changing the orientation of the distal tip relative to the anatomy to, for example, change a view provided by a camera on the distal tip to aim tissue treatment or diagnostic devices advanced from the distal end of the flexible shaft. After use, the entire reusable flexible endoscope must be disinfected which can be a difficult and time-consuming process, especially the working channel of scope shaft. Disposable scope can be discarded, and partial disposable scope can be greener, more economical, providing a new sterile essential, no-worn part for each patient or exchanged during the procedure to provide another feature to treat the same patient.

SUMMARY

The present disclosure relates to an endoscopic device which includes a handle body operatively couplable to a shaft housing. The handle body includes an actuator for controlling a distal end of an endoscopic shaft extending from the shaft housing. The device also includes a pull wire attachment configured to operatively couple to a pull wire extending through the shaft housing and the endoscopic shaft to the distal end. Applying tension to the pull wire deflects the distal end of the endoscopic shaft. In addition, the device includes a pulling mechanism coupled to the actuator and having the pull wire attachment extending therefrom. When the pull wire attachment is operatively coupled to the pull wire, actuation of the actuator applies tension to the pull wire and deflects the distal end of the endoscopic shaft.

In an embodiment, the pulling mechanism is a motor and the actuator is a button pad.

In an embodiment, the pulling mechanism is a pull wheel and the actuator is a deflection knob, wherein rotation of the deflection knob rotates the pull wheel and draws the pull wire attachment proximally and, when the pull wire attachment is operatively coupled to the pull wire, deflects the distal end of the endoscopic shaft.

In an embodiment, the handle body further includes a latch having a latch pin extending radially therefrom, the latch pin being sized and shaped to couple to a pin hole or a slot in the shaft housing.

In an embodiment, either i) the latch extends radially outward from the handle body and the latch pin extends radially inward from the latch or ii) the latch is recessed in the handle body and the latch pin extends radially outward from the latch.

In an embodiment, when the shaft housing comprises the slot, the handle body is rotatable with respect to the shaft housing while maintaining the operative coupling for deflecting the distal end of the endoscopic shaft.

In an embodiment, the device further includes a first electrical connector extending from the handle body, the first electrical connector sized and shaped to make an electrical connection with a second electrical connector in the shaft housing.

In an embodiment, the device further includes a contamination barrier configured to extend from a proximal end of the handle body over a grip portion of the handle body; and a grip configured to expand over the grip portion and the contamination barrier and be tightly fitted to the handle body.

In addition, the present disclosure relates to an endoscopic device which includes a shaft housing operatively couplable to a handle body, the handle body including an actuator; an endoscopic shaft extending distally from the shaft housing, a distal end of the endoscopic shaft having a camera; and a pull wire extending through the shaft housing and the endoscopic shaft to the distal end, wherein applying tension to the pull wire deflects the distal end of the endoscopic shaft, a proximal portion of the pull wire having a sheath surrounding the pull wire and a fitting at a proximal end of the sheath, the fitting being operatively couplable to a pull wire attachment. When the fitting is operatively coupled to the pull wire attachment, actuation of the actuator draws the pull wire attachment proximally, applying tension to the pull wire and deflecting the distal end of the endoscopic shaft.

In an embodiment, the shaft housing includes a pin hole being sized and shaped to couple to a latch pin extending radially from a latch in the handle body.

In an embodiment, the shaft housing includes a slot extending about a portion of a circumference of the shaft housing, the slot being sized and shaped to couple to a latch pin extending radially from a latch in the handle body so that the handle body is rotatable with respect to the shaft housing while maintaining the operative coupling for deflecting the distal tip of the endoscopic shaft.

In an embodiment, the slot is a blind inner diameter radial slot.

In an embodiment, the device further includes a first electrical connector recessed in the shaft housing and sized and shaped to make an electrical connection with a second electrical connector extending from the handle body.

In an embodiment, the first electrical connector is rotatable with respect to the shaft housing.

In an embodiment, the device further includes a contamination barrier configured to extend from a proximal end of the shaft housing proximally over the handle body when the shaft housing and the handle body are operatively coupled.

Furthermore, the present invention relates to a method which includes operatively coupling a handle body to a shaft housing, the handle body including an actuator for controlling a distal end of an endoscopic shaft extending from the shaft housing, the handle body having a pulling mechanism coupled to the actuator and having a pull wire attachment extending therefrom, the operative coupling including coupling the pull wire attachment to a pull wire extending through the shaft housing and the endoscopic shaft to the distal end of the endoscopic shaft; and actuating the actuator so that tension is applied to the pull wire and the distal end of the endoscopic shaft is deflected.

In an embodiment, the pulling mechanism is a motor and the actuator is a button pad.

In an embodiment, the pulling mechanism is a pull wheel and the actuator is a deflection knob. The method further includes rotating the deflection knob to rotate the pull wheel, draw the pull wire attachment proximally and deflect the distal end of the endoscopic shaft.

In an embodiment, the handle body further comprises a latch having a latch pin extending radially therefrom, the latch pin being sized and shaped to couple to a pin hole or a slot in the shaft housing.

In an embodiment, either i) the latch extends radially outward from the handle body and the latch pin extends radially inward from the latch or ii) the latch is recessed in the handle body and the latch pin extends radially outward from the latch.

BRIEF DESCRIPTION

FIG. 4A shows a side view of an endoscope having a connectable and rotatable shaft portion and handle portion according to a second exemplary embodiment of the present disclosure.

FIG. 4B shows a front view of the endoscope of FIG. 4A.

FIG. 11 shows a side view of an internal handle mechanism for pulling an attached pull wire cable and deflect the distal tip FIG. 12 shows an opposing side view of the internal handle mechanism of FIG. 11.

DETAILED DESCRIPTION

Figure 1:
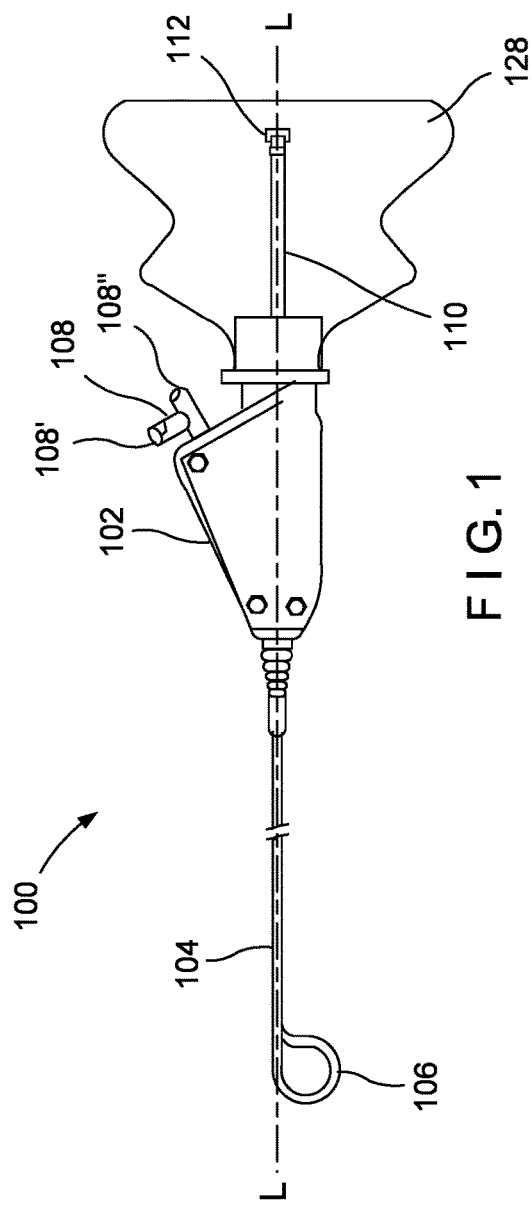
FIG. 1 shows a side view of a connectable shaft portion of an endoscope according to a first exemplary embodiment of the present disclosure.

The present disclosure may be further understood with reference to the following description and the appended drawings, wherein like elements are referred to with the same reference numerals. The exemplary embodiments describe endoscopic devices (e.g., endoscopes) having endoscopic shafts that are separable from their associated endoscopic handles. This permits different types of handles to be connected to different types of shafts. Various embodiments will be described including housing connections, electrical connections, and, in embodiments including scope shafts with a deflectable distal tip, pull wire connections. In some embodiments, the connections between the shaft and the handle allow for rotation of the handle with respect to the shaft. The endoscope may be completely disposable, or to include some components that are reusable while others are disposable. Contamination barriers are also described that may be employed to protect a reusable handle portion or portions from contamination.

The endoscope shown in this disclosure is a digital flexible shaft ureteroscope. However, the exemplary embodiments are not limited thereto and may be adapted to other scope types such as, e.g., digital cystoscopes. For example, a described handle may be compatible with multiple types of shafts, i.e., the same handle may be used in conjunction with a shaft configured for cystoscopy and, in a later procedure, may be combined with a shaft configured for ureteroscopy.

Figure 2:
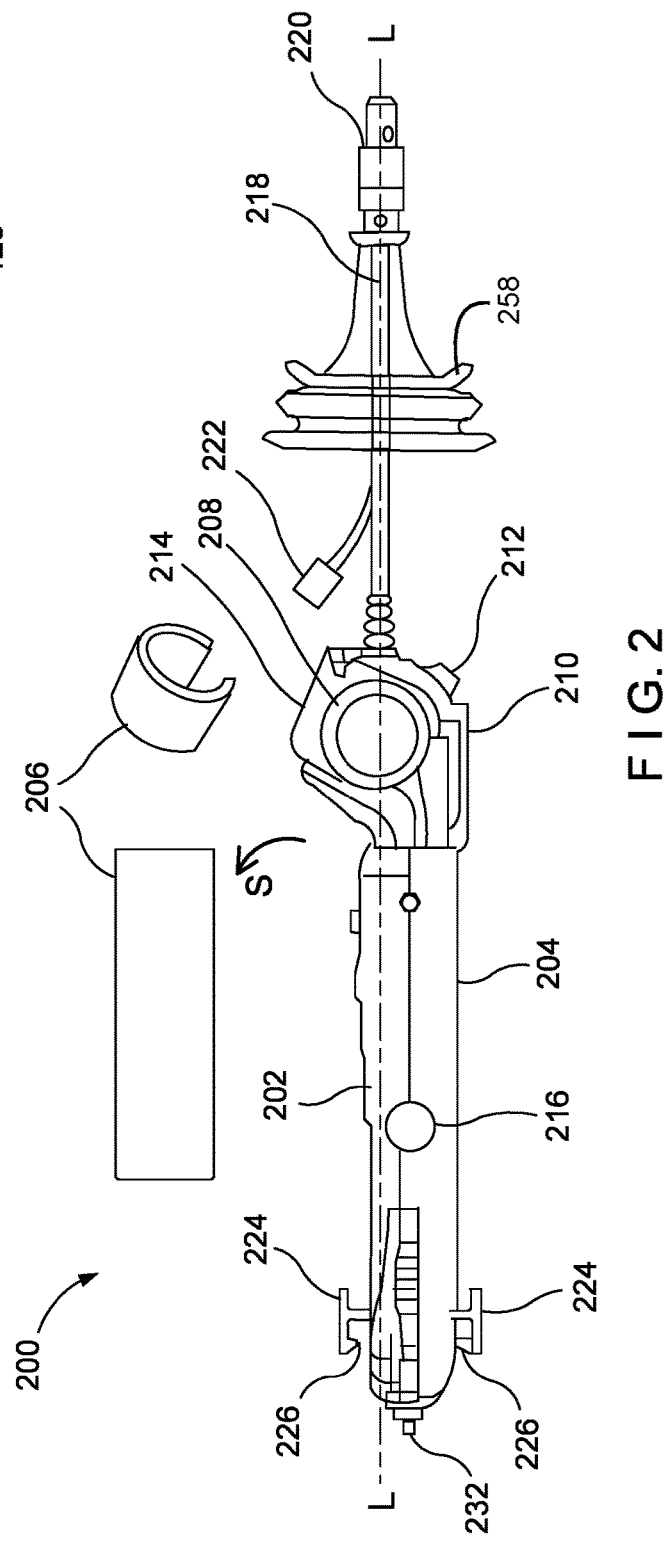
FIG. 2 shows a side view of a connectable handle portion of an endoscope according to a first exemplary embodiment of the present disclosure.
Figure 3:
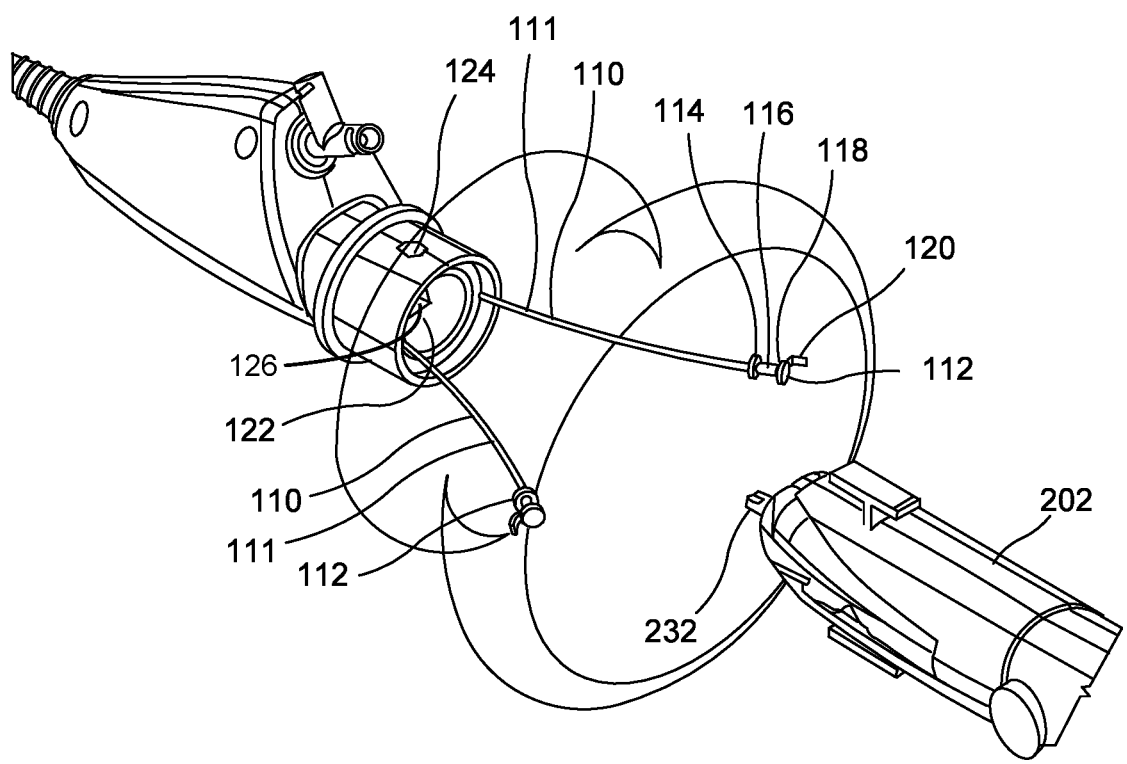
FIG. 3 shows an isometric view of the shaft portion and handle portion of FIGS. 1-2 with cable connectors extending proximally from the shaft portion.
Figure 5A:
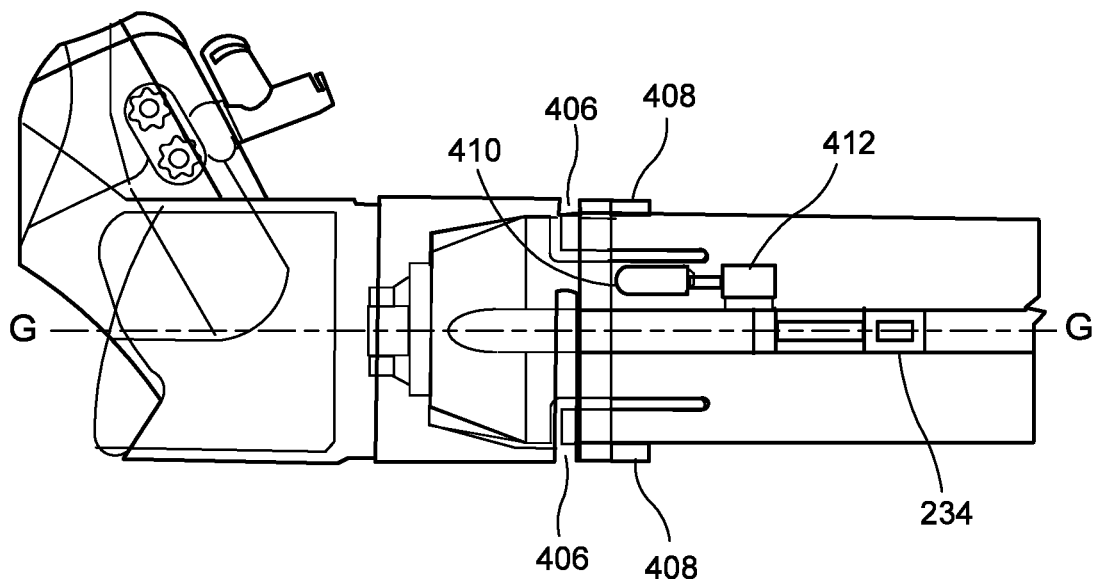
FIG. 5A shows a side view of the endoscope of FIG. 4A with the shaft and handle portions connected and rotated in a first direction.
Figure 5B:
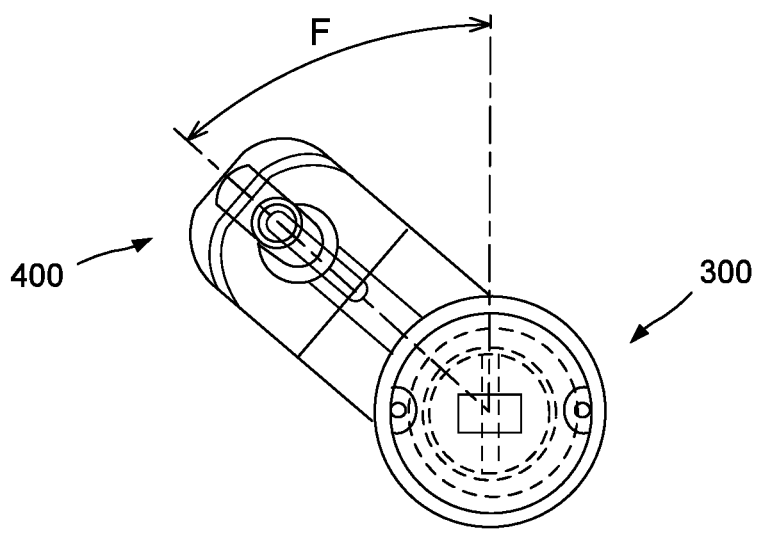
FIG. 5B shows a front view of the rotated endoscope of FIG. 5A.

FIGS. 1-3 show a shaft portion 100 and a handle portion 200 of a connectable endoscope according to various exemplary embodiments of the present disclosure. In the present embodiment, specific connection means for the two parts of the endoscope are described, however, different features described herein may be mixed and matched depending on particular requirements for an endoscopic procedure, in the various manners described below.

The shaft portion 100 includes a shaft housing 102 from which an endoscopic shaft 104 extends distally to a distal tip 106. The endoscopic shaft 104 may include any configuration of working channels such as, for example, be a single lumen working channel, a dual lumen working channel, a larger single lumen working channel (for e.g., kidney stone dusting), or the like. The shaft 104 may include any combination of sensors such as e.g. a pressure sensor, a temperature sensor, etc. or combinations thereof, with connections to these sensors running through the shaft 104, through a working channel or through one or more lumens or clipped to the exterior of the endoscopic shaft 104. The distal tip 106 has a camera which, in this embodiment, has full 270° deflection capabilities in two directions for changing a view of anatomy during the procedure. In other embodiments, the distal tip 106 may deflect in four directions, each 90° apart (i.e., at 0°, 90°, 180°, and 270°). In other embodiments, the shaft 104 may deflect in only a single direction, or in more than two directions.

A T-connector 108 extends from the shaft housing 102 and provides two ports for accessing the one or more working channels of the endoscopic shaft 104. In this embodiment, the first port 108' and the second port 108" are arranged perpendicularly to one another with the first port facing distally and laterally (relative to a longitudinal axis L of the shaft housing 102) and the second port facing proximally and laterally. An accessory device such as e.g. an external flow sensor or additional camera, or an end effector device such as e.g. a kidney stone retrieval device, may be passed through either of the first and second ports 108', 108", however, the second port 108" may be preferred since it is aligned to the working channel of the endoscope shaft. Port 108' is perpendicular to the working channel making the passage of even a flexible elongated device nearly impossible and is used mostly for fluid communication to the working channel. In another embodiment, a Y-connector is used with first and second ports both facing proximally, such that two devices may be passed into the working channel of the endoscopic shaft 104 from a position proximal to the Y-connector.

The handle portion 200 includes a handle body 202 including a grip portion 204 where an operating physician may grasp the handle 200. The grip portion 204 of this embodiment is fitted with a c-shaped or overlapping grip 206 that may be disposed of after use. The overlapping grip 206 may be used over a contamination barrier, to be described in greater detail below. The handle portion 200 may include a magnet coupler 214 for coupling to, e.g., a LithoVue™ Empower™ deployment device for kidney stone retrieval or another accessory device. A power and data cord 218 extends from a proximal end of the body 202 with a connector 220 at an end of the cord 218 for connecting to endoscopic equipment such as a console.

In another embodiment, the handle 200 may be battery-powered and have Bluetooth connectivity so that the power and data cord 218 is not required. In this embodiment, the power and data cord 218 is bifurcated with a communication interface 222 (e.g., a USB connector) extending therefrom. The communication interface 222 may be used to connect, e.g., the LithoVue™ Empower™ deployment device to the handle 200 to power the deployment device and exchange data therewith. Thus, data may pass from an accessory device attached to the handle 200 through the handle 200 and to the console, for example, via the wired power and data cord 218 connection or wirelessly. In other embodiments, accessory devices may run straight from a console connection and bypass the handle 200. In addition, data may pass from the shaft portion 100, e.g., from the camera, to the handle 200 via an electrical connection and then to the console, to be described in further detail below.

A given shaft portion may be coupled to a given handle portion in multiple ways. In the present embodiment, a housing connection is made between the shaft housing 102 and the handle body 202 in the following manner. However, alternative configurations for making a housing connection will be described as well.

The shaft housing 102 defines a recessed portion 122 at its proximal end within which a distal end of the handle body 202 is received when the shaft portion 100 and the handle portion 200 are coupled. In the present embodiment, the handle body 202 includes two latches 224 that are, in this embodiment, substantially T-shaped and which extend radially outward from the body 202 on opposing sides of the body 202. Each of the latches 224 has a latch pin 226 extending radially inward from the distal end of the T-shape, as may be seen in greater detail in FIGS. 9-10. The latch pins 226 are sized to engage corresponding latch pin holes 124 on the shaft housing 102, as may be seen in FIG. 3.

In this embodiment each of the latch pins 226 includes a ramp 228 cut into the pin 226 so that, when the pins 226 are slid distally over the shaft housing 102 and aligned with the latch pin holes 124, the pin ramp 228 facilitates the deflection of the latch pin 226 around the outer surface of the shaft housing 102 until reaching and snapping into the latch pin hole 124. The proximal end 230 of the T-shape may be used as a lever to release the latch pin 226 from the latch pin hole 124 and disengage the handle body 202 from the shaft housing 102 whereupon the handle portion 200 is drawn proximally to release the handle portion 200 from the shaft portion 100. A circular profile for the distal end of the handle body 202 that slides into a circular recess in the shaft housing 102 may be preferred, although it is not required for non-rotational devices. However, a rounded profile allows for compatibility with both rotating and non-rotating devices as will be described in more detail below.

FIGS. 4A-6B show a shaft housing 300 and a handle body 400 utilizing an alternate arrangement for making a housing connection. Among other differences, the handle body 400 uses a recessed pin arrangement. The recessed pin arrangement shown for handle body 400 is not limited to compatibility with the shaft housing 300, i.e., it may be used with differently designed shaft portions in the manner described below.

FIG. 4A shows a handle body 400 with a cantilevered latch 402 cut into a recess 404 in the body 400, the latch 402 having a latch pin 406 for positionally coupling the handle body 400 to a corresponding shaft housing. The latch pin 406 extends radially outward, such that, when the smaller diameter handle body 400 is inserted into the e.g. larger inner diameter shaft housing 300 the latch pin 406 engages the radial slot 302. The handle body 400 may be advanced into the distal shaft body 300 by depressing a latch button 408 positioned along the cantilevered latch 402, thereby deflecting the latch pin 406 radially inward, and releasing the latch button 408 when the latch pin 406 is positioned adjacent to the slot 302.

Although the shaft housing 300 shown in FIG. 4A has the radial slots 302 for receiving the two opposing latch pins 406, a latch pin hole may also be used to receive a recessed pin such as latch pin 406, in a manner similar to that described in FIGS. 1-3 with respect to the shaft portion 100 and the handle portion 200. Whereas FIGS. 1-3 describe a pin directed radially inward engaging a latch pin hole on the outer diameter of the shaft housing, the same principle may be applied to a latch pin directed radially outward engaging a latch pin hole on the inner diameter of a shaft housing.

When a shaft housing has one pin hole for each of two opposing latch pins the shaft housing and the handle body are not rotatably coupled to one another. However, a shaft housing having a slot such as radial slot 302 of shaft housing 300 allows for rotation between a handle portion and a shaft portion, in various manners such as those described below.

FIGS. 4A-6B show the shaft housing 300 having two radial slots 302 for engaging the latch pins 406 of the handle body 400. FIG. 4B shows a cross section of an initial positioning of the shaft housing 300 with respect to the handle body 400, i.e., a non-rotated position. In this embodiment, the slots 302 extend fully through the diameter of the shaft housing 300 and allow for slightly less than 180 deg rotation. In other words, the slots 302 extend around almost the full circumference of the shaft housing 300, with the exception of two small sections of housing delimiting the slots 302 permitting the latch pins 406 to rotate from one edge of the near-180 deg slots 302 to the opposing edge. However, radial slots in another embodiment of the shaft housing may be less than the full 180 deg.

Figure 6A:
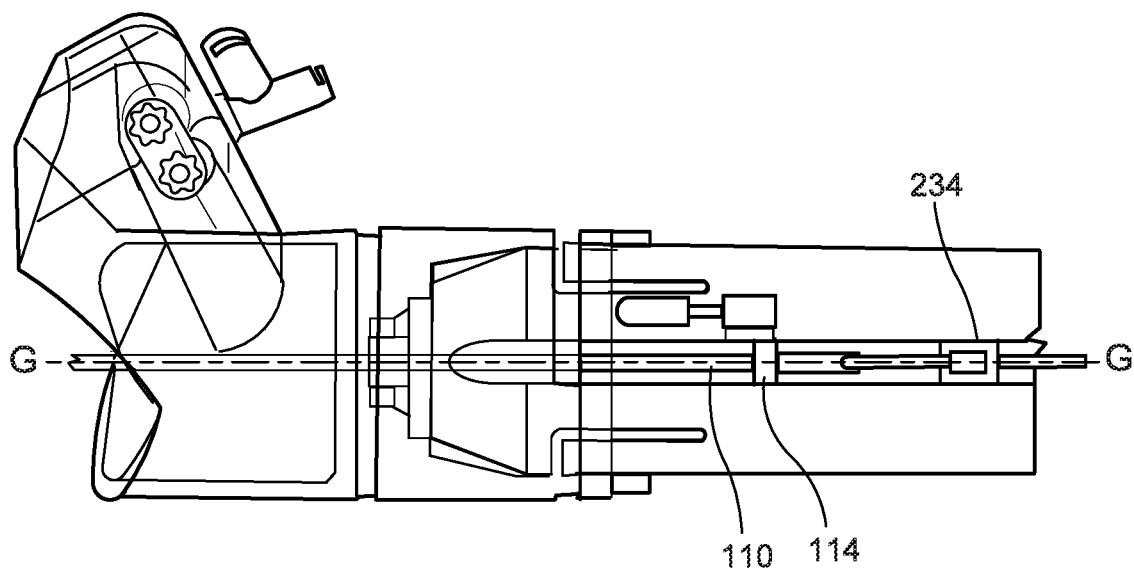
FIG. 6A shows a side view of the endoscope of FIG. 4A with the shaft and handle portions connected and rotated in a second direction.
Figure 6B:
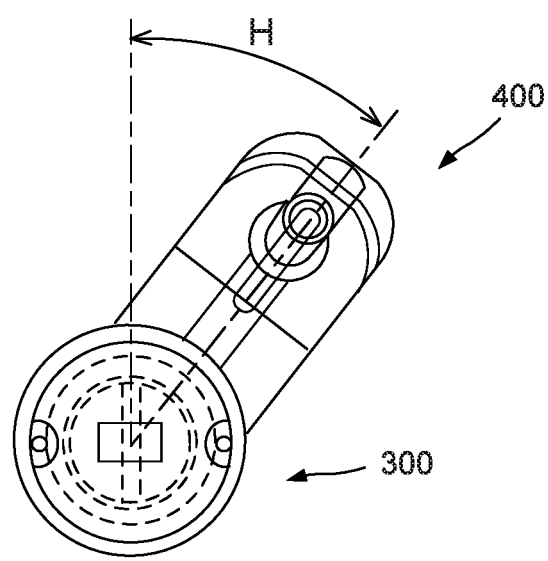
FIG. 6B shows a front view of the rotated endoscope of FIG. 6A.

In the embodiment shown in FIGS. 4A-6B, the shaft housing 300 may also be attached to the handle portion 400 when initially rotated 180 deg about axis G. In this embodiment, if the working channel of the shaft portion is in fluid communication with a T-connector 312, the T-connector 312 is sufficiently angled by the shaft housing to clear the user's grip hand while holding the handle. FIG. 5B shows a cross section of the shaft housing 300 rotated in the direction of the F-arrow with respect to the handle body 400, while FIG. 6B shows a cross section of the shaft housing rotated in the direction of the H-arrow with respect to the handle body 400.

Figure 7:
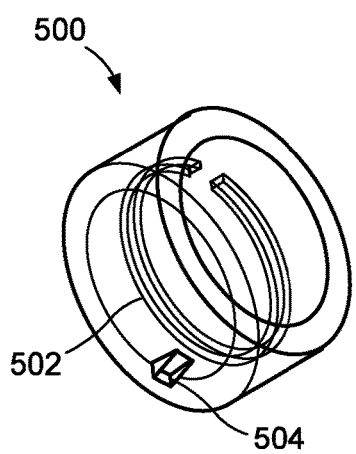
FIG. 7 shows a shaft housing having a blind inner diameter radial slot.

In another embodiment shown in FIG. 7, a radial slot 502 in shaft housing 500 is a blind inner diameter radial C-shaped slot. In other words, the slot 502 extends radially to a depth, and not through the entire wall of the shaft housing 500. In this embodiment, a single latch pin would be used instead of the two latch pins 406 shown with respect to handle body 400. The blind inner diameter radial slot 502 allows for a maximum rotation of nearly 360 deg. In addition, the material behind the blind slot 502 strengthens the structure in addition to covering the slot 502. The shaft housing 500 has an internal ramp 504, to be described further below with respect to an electrical connection. In another embodiment sill referring to FIG. 7. The slot 502 is a helical thread configuration, e.g. 1¼ revolutions allowing the shaft 104 to rotate more than 360° but limiting the rotation to 450°. A Bowden Cable system (pull wire and sheath system) will allow for rotation and extension between a handle portion and a shaft portion while deflecting the flexible shaft 106 as it will be described below.

In still other embodiments, a shaft housing having a radial slot may be selectively lockable so that the user may lock the shaft portion at a desired rotational orientation relative to the handle portion. In one embodiment, as shown in FIG. 4A, the handle body 400 has a pin lock 410 that may be advanced distally via a pin button 412 to couple to a hole lock 304 in the shaft housing 300. In this manner, when the latch pins 406 would otherwise be free to rotate within the slots 302, the pin lock 410 non-rotatably engages the handle body 400 with the shaft housing 300 at a selected rotational orientation. In another embodiment, a shaft housing has a plurality of pin locks around the circumference of the body, such that the shaft housing and the handle may be set at any one of a plurality of selected rotational orientations. In still another embodiment, a pin lock may extend about a portion of the circumference of the shaft housing, such that rotation of the shaft housing is limited to the length of the slot. In other embodiments still, a ratchet, detents, an interference fit or other suitable connection may be used instead of a lock to temporarily hold the rotation of the shaft housing as would be understood by those skilled in the art.

A second connection made when a shaft portion and a handle portion are coupled is an electrical connection. The electrical connection carries electrical power as well as data between the shaft and handle portions. For example, a camera at the distal tip 106 of the endoscopic shaft 104 may exchange data with and be powered by the handle portion 200 via the electrical connection, the handle portion 200 being powered via, e.g., the power and data cord 218 or batteries.

Figure 8:
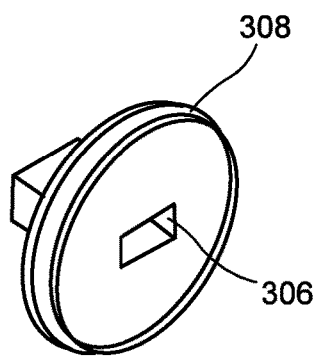
FIG. 8 shows an electrical connector for a rotatable shaft housing.

In the embodiment shown in FIGS. 1-3, a first electrical connector 232 extends distally from the handle body 202 and is sized and shaped to be inserted into a second electrical connector (not shown) at a distal end of the recessed portion 122 of the shaft housing 102. Although the second electrical connector is not shown in the views of FIGS. 1-3, the second electrical connector for the handle body 202 is a recess corresponding to the shape of the first electrical connector 232 and may look similar to the second electrical connection 306 shown in FIG. 8 with respect to the rotatable embodiment.

In the non-rotatable embodiment, the first electrical connector 232 and the second electrical connector may be any shape, i.e., square, rectangular, circular, etc. Because the shaft portion 100 and the handle portion 200 are not rotatable with respect to one another in the present embodiment the electrical connection between the two portions need not be rotatable, unlike the rotatable embodiment to be described below. The second electrical connector 126 is fluid sealed with an O-ring (not shown) to prevent any contamination with fluids from an endoscopic procedure, similar to the O-ring 308 shown in FIG. 8. The O-ring 308 may be molded of prefect parts to create a seal to keep electronics dry when the handle portion 200 is not rotating. In another embodiment, an elastomer seal may be used to create a seal.

In the embodiment shown in FIGS. 4A-6B, the shaft housing 300 and the handle body 400 are rotatable with respect to one another, thus the electrical connection is also rotatable. In this embodiment, the second electrical connector 306 in the shaft housing 300 may be rotated while a first electrical connector 414 in the handle body 400 remains fixed, allowing the entirety of the shaft portion including the shaft housing 300 to rotate with respect to the handle portion including the handle body 400. The rotation of the shaft housing 300 and the handle body 400 is limited such that the pull wires and electrical wires are not twisted off due to continual rotation in one direction.

The second electrical connector 306 is rotationally positioned to couple to the nonrotational first electric connector 414 in the orientation shown in FIGS. 4A-4B. This initial orientation, such as that shown in FIG. 8, may be initially established using an internal ramp 310 in the shaft housing 300, an example of which is shown most clearly in FIG. 7 with respect to internal ramp 504. Although only one internal ramp 310 is shown in FIG. 7, two internal ramps corresponding to two latch pins may be used to mate the handle body 400 to the shaft housing 300, e.g., on opposing sides of the shaft housing 300. The internal ramp 310 may orient the latch pins 406 such that the first and second electrical connectors 414, 306 are properly oriented as well. As the distal end of the handle body 400 is inserted into the proximal end of the shaft housing 300, the pin ramps cause the latch pins to depress into the inner diameter of the shaft housing and then snap/extend into the radial slot 302, creating a lock (preventing movement in the proximal or distal directions) but allowing rotation of the shaft housing 300 and associated shaft relative to the handle.

The handle portion and the shaft portion may be disassembled by depressing the latch buttons 408 to disengage the latch pins 406 from the radial slots 302 and withdrawing the handle body 400 proximally. However, if the shaft is to be reattached later in the procedure, the shaft housing 300 should be rotated back to its initial attachment position before disassembly such that the second electrical connector 306 is rotated to its initial position for later reattachment.

The third connection to be made between a shaft portion and a handle portion is a pull wire connection. This connection is applicable only for endoscopes that have a deflecting distal tip utilizing pull wires for deflecting the distal tip.

The embodiment shown in FIGS. 1-3 includes a motor 208 for implementing the deflection of the distal tip 106 when the distal portion 100 and the handle portion 200 are coupled. The motor 208 may be actuated by a button pad 210 or by a manual deflection knob 212 as would be understood by those skilled in the art. In some instances, the manual deflection knob 212 may act as a backup control means for the distal tip 106 if power to the endoscope is lost during a procedure. In such a situation, if the distal tip 106 is in a deflected position when power is lost, it may be returned to a straight position via the deflection knob 212 prior to removing the shaft 104 from the body. In other instances, only a deflection knob or only a button pad may be used. When accessory devices are used with the endoscope the button pad 210 may be further used to control certain accessory devices. However, control of the distal tip 106 and/or accessory devices may be implemented by other means. For example, an external control means such as a console may be used.

Figure 9:
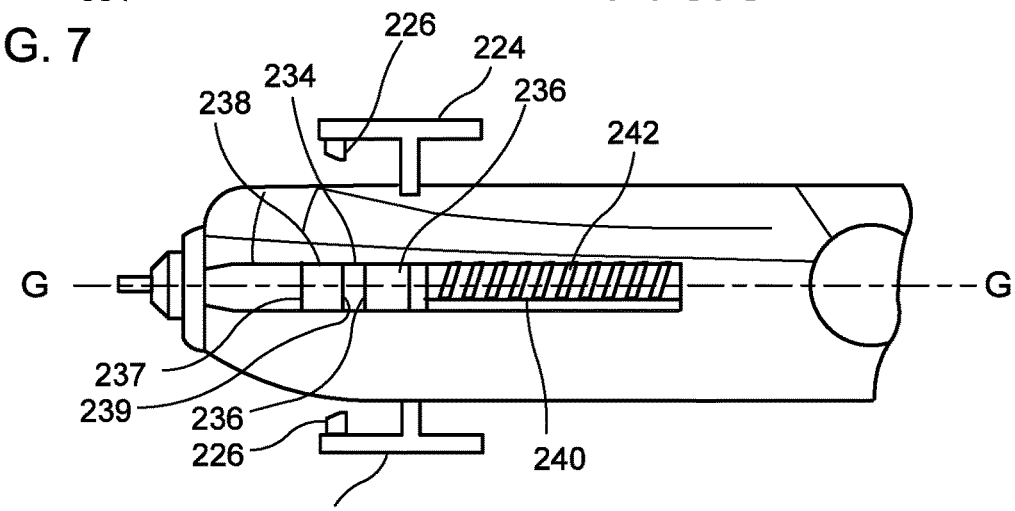
FIG. 9 shows a side view of the handle of FIG. 2 with a mechanism for attaching a pull wire.
Figure 10:
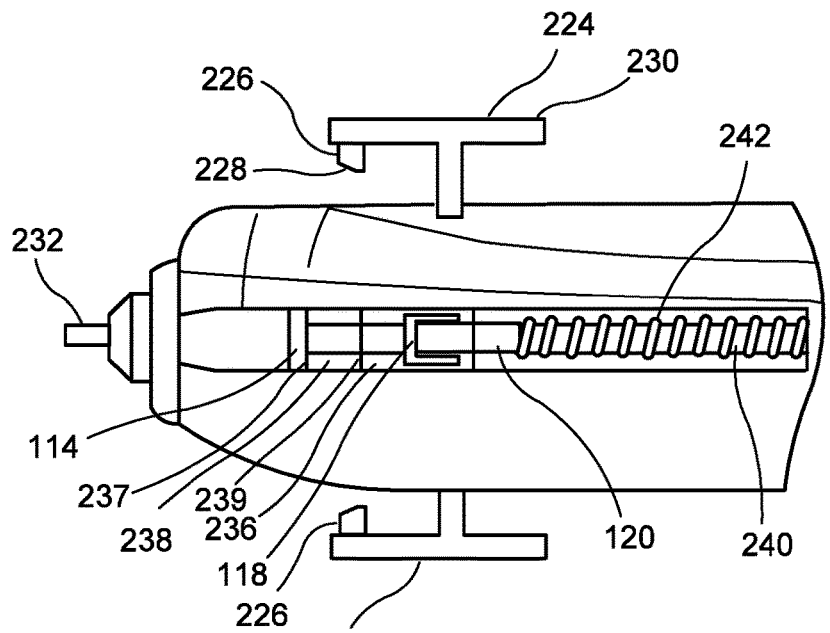
FIG. 10 shows a side view of the handle of FIG. 2 with a pull wire cable from the shaft portion connected to a cable receiver in the handle.

In the embodiment shown in FIGS. 1-3, the distal tip 106 of the endoscopic shaft 104 is deflectable via two pull wires internal to the shaft 104. A single pull wire may deflect the shaft in one direction, while any additional number of pull wires allow for deflection in additional directions (e.g., four pull wires allow for deflection in four directions). The two pull wires of the shaft portion 100 may be connected to the handle portion 200 via two pull wire cables 110 extending out the proximal end of the shaft housing 102. Each cable 110 comprises a sheath 111 surrounding the pull wire within and extends out the proximal end of the shaft housing 102 to a pull wire connector fitting 112 configured to couple with the handle portion 200, as shown in FIGS. 3, 9-10, in a manner to be described in detail below. A length of the sheath 111 may be extended to be attached to a fitting receiver 234, as will be described below. In an embodiment, a distal end of the sheath 111 may be one of a curve, a slack and a bow (similar to FIG. 7) to allow the sheath 111 to wrap around a fitting receiver 234 (described in detail below) as the shaft housing 102 is rotated.

In this embodiment, each of the pull wire fittings 112 includes a distal washer 114, a collar 118 proximal to the washer 114, a spacer 116 separating the washer 114 from the collar 118, and a handle 120 attached to a proximal side of the collar 118. The washer 114 in this embodiment is a smaller diameter disk with respect to the collar 118. The pull wire fitting 112 is attached to the cable 110 by first sliding the washer 114 onto the pull wire so that a distal side of the washer 114 abuts the proximal end of the sheath 111, next sliding the collar 118 (with attached spacer 116) onto the pull wire so that the spacer 116 abuts the proximal side of the washer 114, and attaching the collar 118 to the pull wire. The collar 118 is attached to the pull wire under slight pull wire tension by crimping, soldering, or another suitable attachment means as would be understood by those skilled in the art. The collar 118 and the pull wire are fixed to one another while the washer 114 may be separated from the collar 118. In another embodiment, the sheath 111 and the washer 114 are molded as a single piece. In another embodiment, the pacer 116 and the collar 118 are molded as a single piece.

The pull wire fitting 112 in this embodiment is received by the fitting receiver 234, as shown in FIG. 9. The fitting receiver 234 includes a collar receiver 236 sized and shaped to receive the collar 118 and a stop block 238 distal to the collar receiver 236, the stop block 238 having a distal side 237 and a proximal side 239 with a U-shaped channel extending therethrough to receive the spacer 116 when the pull wire fitting 112 is coupled to the fitting receiver 234. The stop block 238 is built into the handle body 202, i.e., is in a fixed location, while the collar receiver 236 is slidable. The collar receiver 236 may be pulled proximally with respect to the handle body 202.

The collar receiver 236 has a shaft 240 extending proximally therefrom into the handle body 202, a spring 242 surrounding the shaft 240 biasing the collar receiver 236 toward a distal position. The spring 242 extends between the collar receiver 236 and a fixed handle wall 244 that the shaft 240 extends through. Thus, when the collar receiver 236 is pulled proximally, the spring 242 compresses between the collar receiver 236 and the handle wall 244, to be described in greater detail below with respect to FIGS. 11-13.

FIG. 10 shows the pull wire fittings 112 coupled to the fitting receiver 234. The proximal side of the washer 114 is placed adjacent to the distal side 237 of the stop block 238, the spacer 116 extends through the channel in the stop block 238, and the collar 118 is placed into the collar receiver 236. In some embodiments, the collar 118 is snap fitted into the collar receiver 236. If the collar receiver 236 is slid apart from the stop block 238 as the pull wire fittings 112 is being attached, the handle 120 on the collar 118 may be pulled proximally, separating the collar 118 from the washer 114, to fit the collar 118 and the collar receiver 236 together. The handle 120 may also be used to remove the collar 118 from the collar receiver 236 when e.g. the shaft portion 100 and the handle portion 200 are being detached from one another.

When the collar receiver 236 is pulled proximally, the collar 118 snaps into its position between the spacer 116 and the handle 120. The washer 114 abuts the distal side 237 to prevent the sheath 111 from advancing proximally, allowing the collar 118 to separate from the proximal side 239 to displace the pull wire in the proximal direction. The mechanical force or energy is transmitted by the movement of the pull wire relative to the sheath 111. The mechanical force/movement of the pull wire is confined to and follows the path of the sheath 111 to minimize loss of mechanical force.

Figure 13:
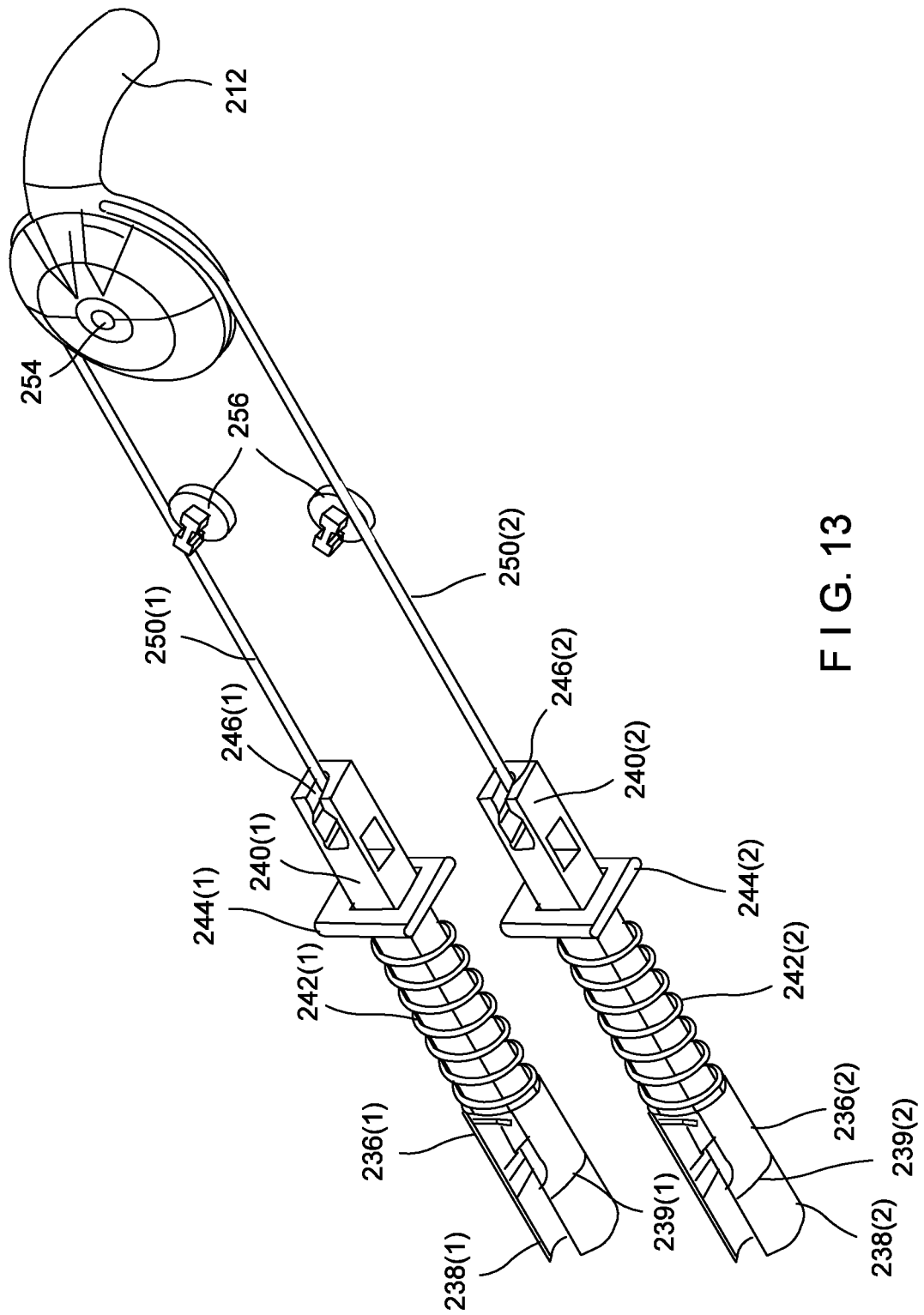
FIG. 13 shows an isometric view of the internal handle mechanism of FIG. 11.

FIGS. 11-13 show a mechanism for pulling the pull wires to control the deflection of the distal tip 106 of the endoscopic shaft 104 when the shaft portion 100 and the handle portion 200 are connected. In this embodiment, the endoscopic shaft 104 has two pull wires for deflecting the distal tip 106 in two opposing directions. Thus, the shaft portion 100 has two cables 100 with pull wire fittings 112 for attachment to two fitting receivers 234 (and associated shafts 240, springs 242, etc.), i.e., a first fitting receiver 234(1) and a second fitting receiver 234(2). The pull wire fittings 112 and the fitting receivers 234 may be color coded or otherwise identified to enable correct connections.

Each of the fitting receivers 234 has a collar receiver 236 with a shaft 240 extending proximally through a hole in the handle wall 244 (i.e., a first shaft 240(1) extends through a first wall 244(1) and a second shaft 240(2) extends through a second wall 244(2)). The proximal ends of the first and second shafts 240(1), 240(2) are coupled by a single robust handle pull wire 250. Each shaft 240 has a pocket 246 and a U-slot 248 of smaller diameter than the pocket 246. To attach the handle pull wire 250 to the shaft 240(1) in this embodiment, a first end of the pull wire 250 is crimped and the first crimped portion 252(1) is received in the first pocket 246(1), with the portion of the handle pull wire 250 proximal to the first crimped portion 252(1) extending through the first U-slot 248(1). In the same manner, a second end of the pull wire 250 is crimped and the second crimped portion 252(2) is received in the second pocket 246(2), with the portion of the handle pull wire 250 proximal to the second crimped portion 252(2) extending through the second U-slot 248(2).

In this embodiment, the pull wires in the endoscopic shaft 104 are controlled by the deflection knob 212. The deflection knob 212 is fashioned with or otherwise attached to a pull wheel 254, the handle pull wire 250 extending about the pull wheel 254. The midpoint of the handle pull wire 250 is fixed to the pull wheel 254 by heat melting, screw, or some other attachment means. The portions of the handle pull wire 250 on either side of the attachment point with the pull wheel 254, i.e., 250(1) and 250(2), are supported between the shafts 240 and the pull wheel 254 by pulley wheels 256. Further, when a first side of the pull wire 250, e.g., pull wire portion 250(1), is under tension and the second side of the pull wire 250, e.g., pull wire portion 250(2), is compressed/ slacked, the pulley wheel 256 prevents unwanted migration of the pull wire portion 250(2) into the interior of the handle body 202.

The pull wheel 254 may be rotated via the deflection knob 212 to deflect the distal tip 106 of the endoscopic shaft 104 in a desired direction and to a desired degree when the shaft portion 100 and the handle portion 200 are fully connected. When the deflection knob 212 is rotated in the direction of arrow N, pull wire portion 250(1) is put under tension and pulls first collar receiver 236(1) proximally, which compressing the spring 242(1) as the collar receiver 236(1) moves proximally. When a first collar 118 is fitted into the collar receiver 236(1) during the proximal pulling, the pull wire in the endoscopic shaft 104 to which the first collar 118 is fitted is also pulled proximally, separating the first collar 118 from the first washer 114 and deflecting the distal tip 106 in a first direction. In other words, the sheath 111 of the first cable 110 remains in a fixed position while the pull wire within is pulled proximally.

On the other side of the pull wheel 254, the second pull wire portion 250(2) compresses/slacks because the shaft 240(2) to which it is attached cannot move in the distal direction, as the second collar receiver 236(2) is abutting the proximal side 239(2) of the second fixed stop block 238(2). In a similar manner, when the deflection knob 212 is rotated in the direction of arrow M, pull wire portion 250(2) is put under tension and pulls the collar receiver 236(2) proximally, thereby pulling the pull wire within second cable 110 proximally, compressing/slacking the first pull wire portion 250(1) and compressing the second spring 242(2) as the first collar receiver 236(1) is abutting the proximal side 239(1) of the first fixed stop block 238(1).

It may be seen that the internal handle mechanism described in FIGS. 11-13 may be applied to a rotatable endoscope as well as a non-rotatable endoscope. That is, rotating the shaft portion 100 would also rotate the orientation of the pull wires within the shaft portion 100. However, the cable connections 110 provide flexibility such that connections between the pull wire fittings 112 and the fitting receivers 234 remain in place, with proximal motion of the fitting receivers 234 still accomplishing the task of pulling the pull wires as described above.

In some embodiments one or two contamination barriers are used to cover the handle and protect it from contamination during use. With respect to FIGS. 1-3, a first contamination barrier 128 is shown at the proximal end of the shaft housing 102 and a second contamination barrier 258 is attached to the proximal end of the cord 218. The second barrier 258 (attached to the cord 218 to cover the handle body 202 from the proximal end) is most often used to protect the handle 200 during shaft exchanges during an endoscopic procedure as the first barrier 128 and the shaft portion 100 are removed/exchanged distally. In other embodiments, the second barrier 258 is used as a safety barrier.

A battery-operated Bluetooth handle would not require a power and a data cord 218, such that the second contamination barrier 258 is then preferred to be closed ended at the proximal end. The other end of the second contamination barrier 258 which is open can be inserted/pulled over the handle body 200 from the proximal end to provide the first layer barrier covering the handle. The first contamination barrier 128 can then be pulled from the distal end to the proximal end over the handle 200 to overlap the second contamination barrier. The C shaped grip 206 can be expanded over both barriers and allow to recover to its nominal state over the handle grip portion to secure the barriers underneath in place. The C shaped grips 206 are disposed after use. The barriers can be loosely or tightly fitted to the handle and can be tied, taped, clipped, banded or the like to the housing, handle or cord. The contamination barrier can be a polymer or an elastomer and can keep contamination out as well as to keep contamination in or contained.

The handle 200 shown may represent different types of handles but are not limited to the handles/features shown, such as an electric motorized handle operated by buttons, a hand operated handle via the deflection knob, etc. Further, in the present embodiment, the handle 200 may convert from a straight grip to a pistol grip (i.e., L-shape) via a pivot joint 216. A portion of the handle 200 proximal to the pivot joint 216 may rotate in the direction of the arrow S with respect to the portion of the handle 200 distal to the pivot joint 216 to transition the handle 200 into the pistol grip.

Similar to the straight grip, the pistol grip may transmit mechanical force or energy by having a channel extending circumferentially around the pulley wheel 256 to maintain the pull wire on the pulley wheel 256 or by using the Bowden cable system. In the Bowden cable system, the sheath 111 confines movement of the pull wire within a lumen of the sheath 111 to transmit mechanical force or energy by the movement of the pull wire relative to the sheath 111. A total length of the sheath 111 is constant, even when the sheath 111 is twisted or moved in the pistol grip, thus allowing movement of the shaft portion 100 and the handle portion 200 relative to each other.

REFERENCE NUMBERS 100 shaft portion
102 shaft housing
104 endoscopic shaft
106 distal tip
108 T-connector
110 pull wire cables
111 pull wire sheath
112 pull wire fitting
114 washer
116 spacer
118 collar
120 handle
122 recessed portion
124 latch pin holes
126 second electrical connector
128 first contamination barrier
200 handle portion
202 handle body
204 grip portion
206 overlapping grip
208 motor
210 button pad
212 deflection knob
214 magnet coupler
216 pivot joint
218 power and data cord
220 connector
222 communication interface
224 latches
226 latch pin
228 ramp
230 proximal end (of latch)
232 first electrical connector
234 fitting receiver
236 collar receiver 237 distal side of stop block
238 stop block
239 proximal side of stop block
240 shaft (collar receiver)
242 spring
244 handle wall
246 pocket
248 U-slot
250 handle pull wire
252 crimped portion
254 pull wheel
256 pulley wheels
258 second contamination barrier
300 shaft housing
302 radial slots
304 hole lock
306 second electrical connector
308 O-ring
310 internal ramp
312 T-connector
400 handle body
402 latch
404 recess
406 latch pin
408 latch button
410 pin lock
412 pin button
414 first electrical connector
500 shaft housing
502 blind slot
504 internal ramp

The invention claimed is:

1. An endoscopic device, comprising:
a handle body operatively couplable to a shaft housing, the handle body including an actuator for controlling a distal end of an endoscopic shaft extending from the shaft housing;
a first electrical connector extending from the handle body, the first electrical connector sized and shaped to make an electrical connection with a second electrical connector in the shaft housing;
a pulling mechanism including a pull wheel coupled to the actuator and a pull wire attachment operatively coupled to a first portion of a pull wire, wherein a second portion of the pull wire extends about the pull wheel and is fixed to the pull wheel at an attachment point, wherein the actuator is configured to apply tension to the first portion of the pull wire to deflect the distal end of the endoscopic shaft, and wherein a pulley wheel supports the first portion of the pull wire between the pull wire attachment and the pull wheel;
a contamination barrier configured to extend from a proximal end of the handle body over a grip portion of the handle body, wherein the contamination barrier terminates proximal to the shaft housing when the shaft housing and the handle body are operatively coupled; and
a grip configured to expand over the grip portion and the contamination barrier, and configured to be tightly fitted to the handle body.

2. The endoscopic device of claim 1, wherein the actuator is a deflection knob, wherein rotation of the deflection knob rotates the pull wheel and draws the pull wire attachment proximally to deflect the distal end of the endoscopic shaft.

3. The endoscopic device of claim 1, wherein the handle body further comprises:

a latch having a latch pin extending radially therefrom, the latch pin being sized and shaped to couple to a pin hole or a slot in the shaft housing.

4. The endoscopic device of claim 3, wherein i) the latch extends radially outward from the handle body and the latch pin extends radially inward from the latch or ii) the latch is recessed in the handle body and the latch pin extends radially outward from the latch.

5. The endoscopic device of claim 3, wherein, when the shaft housing comprises the slot, the handle body is rotatable with respect to the shaft housing while maintaining the operative coupling for deflecting the distal end of the endoscopic shaft.

6. The endoscopic device of claim 1, wherein the grip is releasably coupled to the grip portion of the handle body and the contamination barrier.

7. The endoscopic device of claim 1, wherein the handle body further comprises a pivot joint, wherein a portion of the handle body proximal to the pivot joint is configured to rotate with respect to a portion of the handle body distal to the pivot joint.

8. The endoscopic device of claim 1, wherein the pull wire attachment includes a spring that is compressed when the actuator applies tension to the first portion of the pull wire.

9. An endoscopic device, comprising:
a shaft housing operatively couplable to a handle body, the handle body including an actuator;
a first electrical connector recessed in the shaft housing and sized and shaped to make an electrical connection with a second electrical connector extending from the handle body, wherein the first electrical connector is rotatable relative to the shaft housing;
an endoscopic shaft extending distally from the shaft housing, a distal end of the endoscopic shaft having a camera;
a pull wire extending through the shaft housing and the endoscopic shaft to the distal end, wherein applying tension to the pull wire deflects the distal end of the endoscopic shaft, a proximal portion of the pull wire having a sheath surrounding the pull wire and a fitting at a proximal end of the sheath, the fitting being operatively couplable to a pull wire attachment in the handle body, wherein, when the fitting is operatively coupled to the pull wire attachment, actuation of the actuator draws the pull wire attachment proximally, applying tension to the pull wire and deflecting the distal end of the endoscopic shaft;
a contamination barrier configured to extend from a proximal end of the handle body over a grip portion of the handle body, wherein the contamination barrier terminates proximal to the shaft housing when the shaft housing and the handle body are operatively coupled; and
a grip configured to expand over the grip portion and the contamination barrier, and configured to be tightly fitted to the handle body.

10. The endoscopic device of claim 9, wherein the shaft housing comprises:
a pin hole being sized and shaped to couple to a latch pin extending radially from a latch in the handle body.

11. The endoscopic device of claim 9, wherein the shaft housing comprises:
a slot extending about a portion of a circumference of the shaft housing, the slot being sized and shaped to couple to a latch pin extending radially from a latch in the handle body so that the handle body is rotatable with respect to the shaft housing while maintaining the operative coupling for deflecting the distal end of the endoscopic shaft.

12. The endoscopic device of claim 11, wherein the slot is a blind inner diameter radial slot.

13. The endoscopic device of claim 9, wherein the contamination barrier is a first contamination barrier, the endoscopic device further comprising:
a second contamination barrier configured to extend from a proximal end of the shaft housing proximally over the handle body when the shaft housing and the handle body are operatively coupled.

14. The endoscopic device of claim 13, wherein the grip is configured to expand over the grip portion, the first contamination barrier, and the second contamination barrier.

15. The endoscopic device of claim 9, wherein the actuator is coupled to a wheel and a pull wire in the handle body, the pull wire in the handle body extending about the wheel, wherein the pull wire attachment couples the pull wire in the handle to the pull wire extending through the endoscopic shaft.

16. A method, comprising:
operatively coupling a handle body to a shaft housing, the handle body including:
an actuator for controlling a distal end of an endoscopic shaft extending from the shaft housing,
a pulling mechanism including a pull wheel, a first pull wire attachment, a second pull wire attachment, and a pull wire extending between the first and second pull wire attachments and about the pull wheel, the pull wire being fixed to the pull wheel at an attachment point, the pull wheel and the pull wire being coupled to the actuator, wherein a first portion of the pull wire is on a first side of the attachment point and a second portion of the pull wire is on a second side of the attachment point; and wherein a spring surrounds the first pull wire attachment and is configured to compress when tension is applied to the first portion of the pull wire, and
a first electrical connector extending therefrom,
the operative coupling including:
coupling the first electrical connector with a second electrical connector recessed in the shaft housing,
coupling the first and second pull wire attachments to respective pull wires extending through the shaft housing and the endoscopic shaft to the distal end of the endoscopic shaft, wherein a contamination barrier extends from a proximal end of the handle body over a grip portion of the handle body, the contamination barrier terminating proximal to the shaft housing, and wherein a grip is tightly fitted to the handle body and is expanded over the grip portion and the contamination barrier; and
actuating the actuator so that tension is applied to the first portion of the pull wire in the handle body without applying tension to the second portion of the pull wire in the handle body and the distal end of the endoscopic shaft is deflected.

17. The method of claim 16, wherein the actuator is a deflection knob, the method further comprising:
rotating the deflection knob to rotate the pull wheel, draw the first pull wire attachment proximally and deflect the distal end of the endoscopic shaft.

18. The method of claim 16, wherein the handle body further comprises a latch having a latch pin extending radially therefrom, the latch pin being sized and shaped to couple to a pin hole or a slot in the shaft housing.

19. The method of claim 18, wherein i) the latch extends radially outward from the handle body and the latch pin extends radially inward from the latch or ii) the latch is recessed in the handle body and the latch pin extends radially outward from the latch.

\* \* \* \* \*